United States Patent [19]
Köhler

[11] Patent Number: 4,900,741
[45] Date of Patent: Feb. 13, 1990

[54] COMBINED CIMETIDINE-PIRENSEPINE FORMULATION FOR TREATING PEPTIC ULCERS AND EROSIONS

[75] Inventor: Helmut O. Köhler, Oberursel, Fed. Rep. of Germany

[73] Assignee: BioMed Research Consultants, Ltd.

[21] Appl. No.: 213,359

[22] Filed: Jun. 30, 1988

[51] Int. Cl.[4] .......................................... A61K 31/415
[52] U.S. Cl. .................................................... 514/396
[58] Field of Search ........................................ 514/396

[56] References Cited

PUBLICATIONS

Chem. Abst. (1985)–153135t, vol. 103.
Chem. Abst. (1982)–621K, vol. 96.
Chem. Abst. (1981)–18425p, vol. 95.
Complete Inhibition of Food–Stimulated Gastric Acid Secretion by Combined Application of Pirenzepine and Rainitidine, Gut, 1981, 22, 542–548, Londong, et al.
Simple Approach to Assess Potentiated Drug Combinations in Clinical Trials: Studies With Pirenzepine Plus $H_2$–Receptor Antagonists, International Journal of Clinical Pharmacology, Therapy and Toxicology, vol. 23, No. 6–1985, (pp. 283–287).
Interactions of Cimetidine and Pirenzepine on Peptone–Stimulated Gastric Acid Secretion in Man, Scand. J. Gastroenterol., Suppl., 15 (66), pp. 103–112 (1980), Londong et al.

Primary Examiner—Stanley J. Friedman

[57] ABSTRACT

An orally administered pharmaceutical composition for treating peptic ulcers and other gastrointestinal conditions associated with hyperacidity, which includes both the $H_2$-receptor antagonist cimetidine and the antimuscarinic agent pirenzepine.

14 Claims, No Drawings

COMBINED CIMETIDINE-PIRENSEPINE FORMULATION FOR TREATING PEPTIC ULCERS AND EROSIONS

BACKGROUND OF THE INVENTION

The present invention relates to a novel pharmaceutical composition suitable for treating peptic ulcers and erosions, and other gastrointestinal ailments associated with gastric hyperacidity. More particularly, this invention pertains to an orally administered, pharmaceutical composition comprised of the histamine $H_2$-receptor antagonist cimetidine and the antimuscarinic agent pirenzepine, and a method of using such a pharmaceutical composition to treat gastrointestinal dysfunctions.

It has been recognized that peptic ulcers and erosions can be treated with antimuscarinics, such as atropine, which inhibit the secretion of acid into the stomach. However, the effectiveness of such drugs has been limited by the significant side effects, e.g. increased heart rate, and depressed salivation, which occur at the therapeuttic dosage level.

More recently, it has been observed that selective histamine $H_2$-receptor antagonist, such as cimetidine, and ranitidine, can be used in the treatment of conditions where there is a hypersecretion of gastric acid. These antagonists are distinguished from the drugs commonly known as "antihistamines", e.g. mepyramine, which selectively block the $H_1$-receptors of histamine to inhibit stimulation of the smooth bronchial and other muscles. See, Black et al. (Nature 1972, 236, 385); and Ash and Schild (Brit. J. Pharmacol. Chemother, 1966, 27, 427).

A marked improvement in the healing of peptic ulcers and erosions has been noticed based on the use of the $H_2$-receptor blockers. More recently, the introduction of 24 hour pH-metry has enabled quantitative diagnostic and prophylatic information to be reliably gathered in a short time. Such techniques have demonstrated that the therapeutic effect of the $H_2$-receptor antagonist is related to an increase in luminal gastric pH, particularly between about 11:00 p.m. and 6:00 a.m.

However, the $H_2$-receptor blockers such as cimetidine have also been associated with certain undesirable side effects, including diarrhea and dizziness. Additionally, it is now known that even the continuous 24 hour infusion of high doses of $H_2$-receptor blockers will not induce a continuous 24 hour anacidity or near-neutral pH values in the stomach. Therefore, because it has been demonstrated that blockage of the histamine $H_2$-receptors alone is not effective to eliminate gastric acidity, it has been suggested that the proton secretion associated with peptic ulcers is also induced by factors other than $H_2$-receptor stimulation.

Thus, it would be desirable to provide a pharmaceutical composition for inhibiting the various mechanisms for proton secretion by which gastric hyperacidity results, and which could be administered with reduced undesirable side effects.

At times, particularly in the treatment of the gastric hyperacidity associated with Zollinger-Ellison syndrome, conventional doses of antimuscarinics and $H_2$-receptor antagonists have been given separately to the same patient at the same time. Additionally, Londong et al. reported in Scand. J. Gastroent. 15 (Suppl. 66): 103 (1980) that the combined intravenous injection of the antimuscarinic pirenzepine and the $H_2$-receptor antagonist cimetidine suppressed stimulated acid secretion more than either drug alone. The combined injection was reportedly accompanied by such side effects as blurred vision, dry mouth and weariness.

However, there has been no recognition that the antimuscarinic agent pirenzepine and the $H_2$-receptor antagonist cimetidine should be combined in a single oral formulation for effectively treating peptic ulcers and other gastrointestinal diseases, at lower effective dosages than the dosages at which the separate drug components are conventionally administered, with prolonged therapeutic effect and reduced side effects.

Accordingly, it is an object of the invention to provide an orally administered pharmaceutical composition containing the $H_2$-receptor antagonist cimetidine and the antimuscarinic pirenzepine, which can be used to effectively treat peptic ulcers and the other gastrointestinal conditions associated with hyperacidity, at lower dosages and with less side effects than are associated with the conventional administration of the separate drug components.

Still another object of this invention is the provision of a method for treating peptic ulcers and other gastrointestinal conditions associated with hyperacidity, by orally administering a pharmaceutical composition containing both the $H_2$-receptor antagonist cimetidine and the antimuscarinic agent pirenzepine.

These objects and other advantages of the invention will be apparent from the detailed description which follows.

SUMMARY OF THE INVENTION

The present invention provides an orally administered pharmaceutical composition for treating peptic ulcers and other conditions associated with gastric hyperacidity, which comprises the antimuscarinic agent pirenzepine, and the $H_2$-receptor antagonist cimetidine. The composition is preferably formulated as an orally administered tablet.

The invention is also directed to a method for treating a patient suffering from a peptic ulcer or other condition associated with gastric hyperacidity, including Zollinger-Ellison syndrome, which comprises the step of orally administering an effective amount of a pharmaceutical composition comprising the antimuscarinic pirenzepine and the $H_2$-receptor antagonist cimetidine.

DETAILED DESCRIPTION OF THE INVENTION

While the invention is susceptible to various modifications and alternative forms, the preferred embodiments are described herein in detail. It is to be understood, however, that it is not intended to limit the invention to the specific forms disclosed. On the contrary, it is intended to cover all modifications and alternative forms falling within the scope of the invention.

The present invention provides an orally administered pharmaceutical composition for treating a patient suffering from a peptic ulcer or other ailment associated with gastric hyperacidity, which comprises both the antimuscarinic agent pirenzepine and the $H_2$-receptor antagonist cimetidine. It has been found that the effective dose of the composition contains less antimuscarinic agent and $H_2$-receptor antagonist than the conventionally administered doses of the separate drug components. Because lower dosages of the anti-proton secretion drugs are required, the composition can be administered with reduced side effects. Additionally, patient compliance is encouraged by the lower therapeutic dosage which may be administered as a single dose once daily.

The antimuscarinic agent and H$_2$-receptor antagonist used in the invention safely decrease proton secretion into the stomach lumen, particularly at night, thereby presumably preventing or promoting the heating of peptic ulcers and erosions, and other conditions associated with gastric hyperacidity. Although the drug components of the composition can exist as addition salts, reference will be made throughout this specification, for convenience, to the parent compound.

The antimuscarinic agent pirenzepine which is employed in the invention is a tricyclic gastric-acid inhibitor commercially available from Boehringer. The preparation of pirenzepine is described in Fr. Patent No. 1,505,795 (1967), which is incorporated by reference herein. Pirenzepine is conventionally administered alone at a recommended daily dosage of 2.0 to 3.0 mg per kg body weight, or 100-150 mg per adult patient in 2-3 divided doses.

The preparation of the histamine H$_2$-receptor antagonist cimetidine which is used according to the invention is described in U.S. Pat. No. 3,950,333 (incorporated by reference herein). Cimetidine is commercially available under the brand name Tagamet® from Smith, Kline and French. When administered alone, the recommended daily dosage of cimetidine is 24 to 32 mg per kg body weight or 1.2-1.6 g/patient in 4 divided doses.

The weight ratio of pirenzepine to cimetidine in the pharmaceutical composition of the invention is preferably from about 1:12 to about 1:5, and is most preferably about 1:12. The composition is preferably used in adult daily dosage amounts which include about 300 mg cimetidine and about 25 mg pirenzepine, administered b.i.d., or about 600 mg cimetidine and about 50 mg pirenzepine, administered o.d. The recommended daily dosage preferably contains about 600 mg of cimetidine and about 50 mg of pirenzepine, per about 50-60 kg of body weight.

The actual therapeutic dosage will of course depend on such factors known to those of ordinary skill in the art, including the age and weight of the patient, the route of administration, and the type of gastrointestinal condition from which the patient suffers. In any event, the composition will be administered at dosages and in the manner which the patient's attending physician deems calculated to deliver an effective amount of the composition based upon the patient's unique condition.

The composition of the invention is administered orally in a suitable form such as a tablet, syrup or elixer, or suspension. The composition is preferably orally administered in the form of a tablet.

Tablets intended for oral use may be prepared according to any method known to the art for the manufacture of pharmaceutical composition, and such tablet may contain one or more agent selected from the group consisting of sweetening agents, flavoring agents, coloring agents, and preserving agents, in order to provide a more palatable preparation. Tablets prepared according to the invention can also contain other nontoxic pharmaceutically acceptable excipients and fillers which are suitable for the manufacture of tablets. Such excipients include inert diluents, binding agents, lubricating agents, and others known to those skilled in the art. The tablets may be uncoated or may be coated by known techniques to delay disintegration and absorption in the gastrointestinal tract, thereby providing a sustained action over a longer period.

The pharmaceutical composition is preferably tableted or otherwise formulated to include the daily dosage in 1-2 tablets. In other words, the composition is preferably formulated so that it need only be administered once daily, in order to ensure better patient compliance.

The pharmaceutical composition of the invention may be used to treat or prevent a variety of gastrointestinal dysfunctions. As used herein, the phrase "gastrointestinal dysfunction" includes peptic ulcers and other conditions associated with gastric hyperacidity. For example, the composition may be used to treat peptic ulcer or erosion disease of the esophagus, stomach, and duodenum. Alternatively, the composition may be used to treat Zollinger-Ellison syndrome, or to treat or prevent the hyperacidity, and/or peptic ulcers (including bleeding therefrom) which frequently results from neurosurgery, head injury, severe body trauma, and burns.

The invention will be further described by reference to the following detailed example, which is not intended to be limiting, but rather illustrative of some approaches taken. This example may, of course, be varied in accordance with the spirit and scope of this illustration.

EXAMPLE

Tablets having the following composition were prepared:

| | |
|---|---|
| Cimetidine (Richter, Budapest) | 300 mg |
| Pirenzepine.HCl (Ind. Chimiche Italiane) | 25 |
| Microcrystalline cellulose (Avicel PH 101) | 75 |
| Starch | 40 |
| Polyvinylpyrrolidone | 25 |
| Hydroxpropylcellulose (KLUCEL HF) | 0.7 |
| Talcum | 15.3 |
| Magnesium stearate | 6.1 |
| Ultra-amylopectin | 15.3 |
| Microcrystalline cellulose (Avicel PH 102) | |
| Total per one tablet | 511.0 mg |

Healthy, informed volunteers, male and female, ate nothing after a noon light lunch. At 5:00 p.m., an Ingold pH electrode-probe was inserted intranasally, and the intragastric location of the tip was demonstrated by the sudden change from a pH of about 6.6 in the oesophagus to a pH of less than 1.7 when the tip entered the stomach lumen. The probe cable was taped to the subject's face, passed over the ear (left side on all occasions) and connected to an Autronic pH-metry apparatus, or a Gastrograpth Mark I machine, in a carrying case at hip level (see C. J. Fimmel et al., *Gastroenterology*, 88, 1842, 1985).

Digital pH measurements were made from 6:00 p.m. to 7:00 a.m. the next morning. In Experiment I, at precisely 6:00 p.m. the subjects orally took 2 tablets of cimetidine-pirenzepine (formulated as described above) with about 250 ml water. In Experiment II, the subjects instead took 600 mg of cimetidine (SmithKline) alone in tablet form for comparison, in the same volume of water as in Experiment I. In Experiment III the subjects took 50 mg pirenzepine (Boehringer) along with 250 ml water for comparison.

At precisely 7:00 p.m. the subjects had a standardised evening meal consisting of a two-egg omelette and 250 ml milk. No further oral intake was allowed until after the electrode probes were removed for recalibration at 7:00 a.m. the next morning. There were no noticeable side-effects experienced from the drugs whatsoever, and both nights involved quiet, undisturbed sleep with no serious discomfort from the electrode cables. Each subject served as his/her own control by participating in all experiments on consecutive days. The experiments were double bond but not randomized.

Each volunteer was subjected to all three experiments. It was determined that the administration of each drug was accompanied by a transient increase in pH above the subject's night baseline pH. Mean baseline values for each subject were determined by comparing the pH values before and after onset of the drug-induced increase in pH.

The pH values measured over time were used to calculate the data reported in the Table which follows, i.e. peak pH values, total durations of pH increase until return to baseline, areas-under-the-curve (pH increase vs time), and the percentages of total pH values above a given value over a period of 12 hours. All figures reported in the table are mean values and the "*" symbol is used to indicate statistical significances ($P<0.05$).

TABLE

|  | Exp. I (cim. & pirenz.) | Exp. II (cim. alone) | Exp. III (pirenz. alone) |
| --- | --- | --- | --- |
| Baseline pH | 0.825 | 1.0 | 0.85 |
| Peak pH response | 6.55* | 5.3* | 5.0* |
| Delta pH response | 5.73* | 4.3* | 4.15* |
| Total duration (h) | 5.6 h.* | 4.4 h.* | 3.6 h.* |
| Area-under-the curve (pH vs. time) | 123.5* | 91.3* | 85.7* |
| 75% total data (pH) | >1.45 | >1.35 | >1.40 |
| 50% total data (pH) | >2.4* | >1.65* | >1.58* |
| 25% total data (pH) | >5.55* | >2.35* | >2.28* |
| Total pH values >5.5 | 25% | 4.5% | 4.1% |

The data provided in the above table should be considered in view of the logarithmic basis for pH values. For example, an increase in peak pH value of 1.2 units corresponds to a greater than tenfold decrease in proton concentration. The data in the above table clearly show that the combined cimetidine/pirenzepine treatment was far more effective than either cimetidine or pirezepine alone in the following aspects.

When compared with the administration of cimetidine alone, the combined formulation produced a 32.3% higher peak pH response, a 27.3% longer duration of action, and a 35.3% greater overall response (as measured by area-under-the-curve), and also resulted in 25% of the total measured pH data over 12 hours being greater than 5.5. In contrast, only 4.5% of the total measured pH data, over the same time period, was greater than 5.5 when cimetidine was given alone. The comparisons of the combined formulation vs. pirenzepine alone showed even greater differences.

The above data demonstrate that the combined oral formulation provides an increased and prolonged therapeutic effect, and can therefore presumably be administered at lower effective dosages, in comparison with the separate drug components.

What is claimed is:

1. An orally administered pharmaceutical composition in dosage form for treating gastrointestinal dysfunction, consisting essentially of an orally effective amount of cimetidine and an orally effective amount of pirenzepine in proportions effective to treat gastrointestinal dysfunction.

2. The composition according to claim 1 which is in an effective o.d. dosage form comprising about 600 mg cimetidine and about 50 mg pirenzepine.

3. The composition according to claim 1 which is in an effective b.i.d. dosage form comprising about 300 mg cimetidine and about 25 mg pirenzepine.

4. The composition according to claim 1 which is in the form of an orally administered tablet.

5. The composition according to claim 1, wherein the tablet further comprises a neutral filler material.

6. A method for treating a patient for gastrointestinal dysfunction which comprises orally administering to the patient a pharmaceutical composition in dosage form, consisting essentially of an orally effective amount of cimetidine and an orally effective amount of pirenzepine in proportions effective to treat gastrointestinal dysfunction.

7. The method according to claim 6, wherein the composition is administered once daily in an effective o.d. dosage form comprising about 600 mg cimetidine and about 50 mg pirenzepine.

8. The method according to claim 6, wherein the daily dose is divided and administered b.i.d.

9. The method according to claim 6, wherein the composition is administered twice daily in an effective b.i.d. dosage form comprising about 300 mg dimetidine and about 25 mg pirenzepine.

10. The method according to claim 6, wherein the composition is orally administered in the form of a tablet.

11. The method according to claim 10, wherein the tablet further comprises a neutral filter material.

12. The method according to claim 6, wherein the patient suffers from a peptic ulcer or erosion.

13. The method according to claim 6, wherein the patient suffers from gastric hyperacidity.

14. The method according to claim 13, wherein the gastric hyperacidity results from Zollinger-Ellison Syndrome.

* * * * *

UNITED STATES PATENT AND TRADEMARK OFFICE
CERTIFICATE OF CORRECTION

PATENT NO.  :  4,900,741
DATED       :  FEBRUARY 13, 1990
INVENTOR(S) :  Kohler, Helmut O.

It is certified that error appears in the above-identified patent and that said Letters Patent is hereby corrected as shown below:

On the cover page in the title delete "PIRENSEPINE" and insert --PIRENZEPINE--;

Column 1, line 2, delete "PIRENSEPINE" and insert --PIRENZEPINE--;

Column 1, lines 21-22, delete "therapeuttic" and insert --therapeutic--;

Column 1, line 24, delete "antagonist" and insert --antagonists--;

Column 5, line 44, delete "pirezepine" and insert --pirenzepine--;

Claim 9, line 3 (column 6, line 40), delete "dimetidine" and insert --cimetidine--.

Signed and Sealed this

Twenty-first Day of May, 1991

Attest:

HARRY F. MANBECK, JR.

Attesting Officer

Commissioner of Patents and Trademarks